United States Patent [19]
Beauducel et al.

[11] Patent Number: 5,549,008
[45] Date of Patent: Aug. 27, 1996

[54] DEVICE AND METHOD FOR CHARACTERIZING A MEDIUM COMPRISING AT LEAST A CONDUCTIVE PART

[75] Inventors: Claude Beauducel, Henouville; Didier Frot, Choisy Le Roi; Pierre Gonzalez, Rueil Malmaison, all of France

[73] Assignee: Institut Francais du Petrole, Rueil Malmaison, France

[21] Appl. No.: 167,347

[22] Filed: Dec. 15, 1993

[30] Foreign Application Priority Data

Dec. 15, 1992 [FR] France .................................. 92 15112

[51] Int. Cl.⁶ .............................. G01F 1/74; G01N 27/74
[52] U.S. Cl. ........................................ 73/861.04; 324/204
[58] Field of Search ........................ 73/861.04; 324/228, 324/234, 236, 239, 204

[56] References Cited

U.S. PATENT DOCUMENTS

| | | | |
|---|---|---|---|
| 3,292,077 | 12/1966 | Sloughter ................................. | 324/204 |
| 3,715,919 | 2/1973 | Kishimoto et al. ..................... | 324/204 |
| 3,916,926 | 11/1975 | Smolin et al. ........................... | 324/204 |
| 4,059,795 | 11/1977 | Mordwinkin . | |
| 4,282,487 | 8/1981 | Warren et al. ........................... | 324/204 |
| 4,367,440 | 1/1983 | Mazzagatti . | |
| 4,429,581 | 2/1984 | Furmaga . | |
| 4,432,951 | 2/1984 | De Schepper et al. ................... | 423/89 |
| 4,523,146 | 6/1985 | Champaigne ........................... | 324/204 |

FOREIGN PATENT DOCUMENTS

| | | |
|---|---|---|
| 0393359 | 10/1990 | European Pat. Off. . |
| 2319115 | 2/1977 | France . |

*Primary Examiner*—Richard Chilcot
*Assistant Examiner*—Harshad Patel
*Attorney, Agent, or Firm*—Antonelli, Terry, Stout & Kraus

[57] ABSTRACT

The present invention relates to a method and to a device for testing a partly conductive medium to determine a characteristic thereof. A signal generator generates a periodic excitation signal in a resonant circuit, including a coil which produces a magnetic field, which is coupled to the partially conductive medium. Eddy currents induced in the partially conductive medium cause the current flowing in the resonant circuit to vary. The amplitude of the envelope of the current flowing in the resonant circuit is measured and processed to determine the characteristic of the medium.

25 Claims, 4 Drawing Sheets

DEVICE AND METHOD FOR CHARACTERIZING A MEDIUM COMPRISING AT LEAST A CONDUCTIVE PART

BACKGROUND OF THE INVENTION

FIELD OF THE INVENTION

The present invention relates to a device and to a method allowing, from the (Eddy) current losses generated in a partly conductive medium or body, for at least a characteristic of the medium to be obtained.

The present invention may be applied for testing characteristics of a medium or part of a medium having a low conductivity value, this value being translated into low Foucault current values.

The invention is particularly applicable to the production of effulent, where the phases contained in an effluent comprising for example a low-conductivity aqueous phase, an organic phase and a gas phase are generally to be tested or measured.

It may therefore be applied to the determination of the amounts or flow rates of the hydrocarbon components constituting these three distinct phases contained in a single volume, with these measurements being generally difficult to obtain continuously.

The invention may be particularly applied to oil production, where the amounts or the flow rates of the hydrocarbon components contained in a single volume are generally desirable to measure these components constituting three distinct phases which are difficult to analyze continuously.

This invention may be applied more particularly within its scope to crude dehydration, environmental protection or crude storage control.

The invention further allows, in the case of fluid storage management, the separation dynamics of the phases constituting a fluid contained in a single volume to be measured, one of these phases being conductive, and in particular to know the decantation time of the fluid.

The invention may also be of use in the measuring of the level or of the volume of the conductive phase of a fluid, notably for a liquid conductive phase, the fluid being contained in a determined volume or flowing in a pipe.

DESCRIPTION OF THE PRIOR ART

Conventional techniques for detecting a characteristic of a conductive medium representative of its conductivity require capacitive detectors and are therefore intrusive.

U.S. Pat. No. 4,717,600 mentions a known device for obtaining information of the nature of coins by observing the decrease in the Foucault currents generated by a variable magnetic field. This device works by sending continuously successive of impulses of constant voltage in a coil or inductance and then observing the relaxation time of the excited system. It does therefore not allow the nature of the coins to be determined continuously.

Furthermore, the non-uniform nature of the magnetic field generated at the end of the coil makes the quantitative analysis of the dissipations due to the Foucault currents inaccurate and difficult.

SUMMARY OF THE INVENTION

The device and the method according to the invention allow at least a slightly conductive part of a medium consisting of several phases of different conductivities to be tested without being affected by possible disturbances due to the outside environment.

The invention makes use of the fact that a partly conductive medium or body, located close to an inductive device such as a coil through which an alternating current flows, has induced currents or Foucault currents flowing therein which lead to efficiency losses, i.e. a decrease in the value of the quality factor Q of an activated resonant circuit in which the coil is included, and notably in the amplitude variation of the voltage at the coil terminals.

The method according to the invention thus allows a characteristic of the partly conductive body to be directly determined from the amplitude variation of a signal envelope measured at the coil terminals.

The present invention relates to a method for obtaining a characteristic of a medium or a body comprising at least a conductive part. The presence of the partly conductive body is detected by measuring for example one of its characteristics through the measurement alone of the amplitude variation of the signal measured at the terminals of a resonant inductive circuit excited by a periodic excitation signal whose frequency is substantially equal to the value of the tuning frequency of the resonant circuit or specific pulsation frequency of the circuit.

A characteristic of the body containing at least a conductive part is detected for example through the amplitude variation of the signal measured at the terminals of a resonant inductive circuit excited by a periodic excitation signal whose frequency is substantially equal to the value of the tuning frequency of the resonant circuit or specific pulsation of the circuit.

The periodic excitation signal may be a continuous signal.

The periodic excitation signal may consist of pulse trains of fixed durations.

When the body is a fluid comprised of a conductive phase whose volume is known and a non conductive phase, the average conductivity of the conductive phase may be determined.

When the body is a fluid comprised of at least a conductive phase of known conductivity and of at least a non conductive phase, the volume of the conductive phase of said fluid may be determined.

The mass flow rate of the conductive phase may for example be determined for a fluid consisting of several phases among which at least one is conductive with the fluid flowing in a pipe running at least partly in the vicinity of the inductive circuit.

When the phases have substantially identical velocities of flow, the volume flow rate of the fluid may be determined.

When the body is a fluid of known volume contained in a vessel with at least part of the fluid passing in the vicinity of the inductive circuit, the fluid comprising at least two liquid phases, with one of the two phases being a conductive phase, the level of the conductive phase of the fluid in the vessel may be determined.

When the body is a fluid consisting of two liquid phases in an emulsion with the fluid being located at least partly in the vicinity of the inductive circuit, the decantation time of the fluid may be determined, i.e. the time passage between a moment when the fluid is in total emulsion and the moment when the liquid phases constituting the fluid are separated.

The present invention relates to a device for implementing the method according to the invention. It comprises in combination inductive means such as a coil, means such as a signal generator for generating a periodic excitation signal for inducing a voltage in the inductive means, means such as a detector for measuring an amplitude variation of the signal measured at the terminals of the inductive means, due to the presence of a partly conductive body located close to the inductive means, and a processor for determining directly, from the amplitude variation of the signal, a characteristic of the partly conductive body.

The body is for example located inside the inductive means.

The inductive means may include a transmitter-receiver coil.

The transmitter-receiver coil includes for example a double winding for generating a uniform electromagnetic field inside the coil.

The method may be applied for testing a petroleum effluent having at least a conductive phase and a non conductive phase, and the conductive phase may be an aqueous phase such as salty water.

The device and the method according to the invention are advantageous in that they are simpler and less expensive since only one coil is used as a transmitter-receiver.

The geometry preferably selected for the device, which consists in positioning the analyzed medium inside the coil, also allows a qualitative analysis of the medium to be performed since the magnetic field created is homogenous, i.e. the field lines used for analyzing the medium are evenly distributed around the coil.

BRIEF DESCRIPTION OF THE DRAWINGS

Other features and advantages of the invention will be clear from reading the description hereafter of embodiments given by way of non limitative examples, with reference to the accompanying drawings in which.

DESCRIPTION OF THE PREFERRED EMBODIMENTS

The description hereunder relates more particularly, but in a non limitative way, to a body having a fluid medium comprising at least an aqueous phase such as water having a low conductivity and a non conductive organic phase, for example oil, when the fluid is a hydrocarbon or petroleum effluent.

The invention utilizes the fact that a partly conductive medium or body located close to an inductive device such as a coil through which an alternating current flows contains induced currents or Foucault currents which lead to efficiency losses, i.e. a decrease in the value of the quality factor of an activated resonant circuit in which the coil is included.

The method according to the invention allows a characteristic of the partly conductive body to be determined from the variation in the quality factor of the activated resonant circuit.

The quality factor varies inversely to the conductivity value of a body or of a medium, i.e. inversely to an amount of conductive part or phase in the medium.

Figure 1:
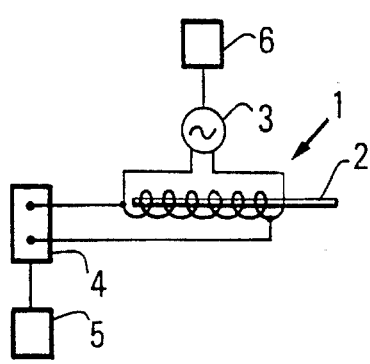
FIG. 1 is a diagram of the device according to the invention including a single coil.

The device for implementing the method includes (FIG. 1) an inductive circuit comprising an inductive coil 1 in which a partly conductive body 2 is for example placed.

A signal generator 3 allows a periodic excitation signal, for example an alternating signal, to be sent to the coil 1, generating therein a periodic current which produces Foucault currents inside the body 2. Measuring means 4, such as a detector, connected to coil 1 detect an amplitude variation of an envelope of the alternating signal measured at the terminals of coil 1 and a variation in the quality factor of the activated resonant circuit. The detector 4 transmits a signal representative of this variation to a processing means 5 such as a programmable processor allowing the characteristic of the partly conductive body to be directly obtained from the signal measured.

The conductive body 2 comprising a conductive part is preferably located inside the coil so as to carry out measurements in a homogenous magnetic field due to the field lines inside the coil.

The "resonant circuit" is the electronic circuit constituted by generator 3, the inductive coil and possibly other elements located in the circuit.

The device further includes a device 6 for controlling signal generator 3 which allows the parameters of the alternating signal sent into coil 1 to be selected.

The device also comprises measuring device 4, a control system (FIG. 2) for selecting the frequency for which the amplitude variation measurements are performed. In a preferred embodiment, the value of the working frequency is so selected that the tuning frequency of the resonant circuit is contained in a range centered on the value fo of the generator frequency. The range is preferably equal to:

$$fo \pm fo/Q,$$

fo=generator frequency,

Q=quality factor.

The tuning frequency corresponds notably to the specific pulsation of the circuit.

The control system is therefore notably used to adjust the value of the tuning frequency of the resonant circuit so that it is subtantially equal to the generator frequency.

In order to improve the measurement accuracy, the parameters of coil 1, i.e. its self-induction coefficient L, its capacitive value C and its resistance r, are so selected that the value of the ratio (L/r) is the highest possible value.

In order to have a constant electromagnetic field inside the coil, the latter is preferably made by using the known double winding technique.

Figure 2:
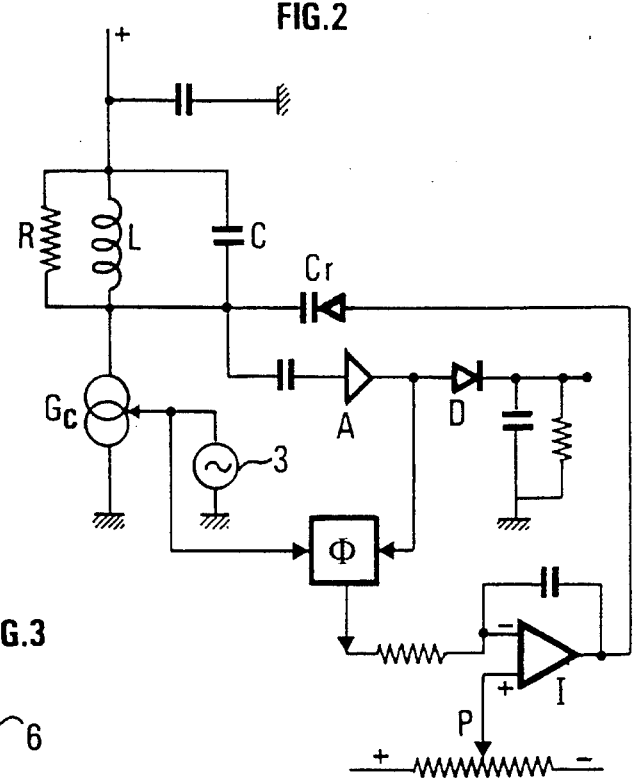
FIG. 2 diagrammatically shows an embodiment of a circuit including an inductive part according to the invention, a signal generator for generating currents, a detector for measuring the amplitude of the signal envelope and a frequency control for controlling a tuning frequency of resonance.

FIG. 2 diagrammatically shows an example of a possible mounting for the inductive elements and the various elements constituting the resonant circuit, the control system and the measuring means.

The resistance R in FIG. 2 schematizes the value of the resistance of coil 1 and of the resistances generated by the losses due to the Foucault currents in the conductive body.

The parameters L and C refer respectively to the self-induction coefficient of the coil and to its parasitic capacitance.

Reference $C_r$ represents a variable capacitance allowing the frequency of the circuit to be changed to the frequency of the signal applied by the generator.

A signal generator 3 controls a current generator Gc connected to the coil. The serial mounting of the generator with resistance R allows the value of the inner resistance of generator 3 to be neglected with respect to the resistance R partly representative of the measurement of the losses generated in the body by the Foucault currents.

The detecting device 4 for measuring the amplitude of the envelope of the alternating signal measured at the terminals of the resonant circuit includes for example a buffer amplifier A and a rectifier diode D, the diode being followed by a circuit allowing the signal to be filtered and more particularly an average value, also called an envelope value of the signals converted by the diode, to be established. The lay-out of such elements is well-known.

The control system for controlling the tuning frequency of the resonant circuit includes a phase comparator Φ connected to the current generator Gc delivering the excitation current to the coil and to the output of buffer amplifier A through conventional electric connection. Phase comparator Φ delivers a voltage proportional to the phase difference between the current injected into the resonant circuit and the phase of the voltage of the measured signal. An integrator I located after phase comparator Φ and connected to the variable capacitance $C_r$ integrates the phase difference and controls the capacitance $C_r$ in order to determine the tuning frequency, so that its value is substantially equal to the frequency value of the generator.

This control is automatically adjusted so that the output voltage of the phase comparator is substantially equal to a set value imposed by the adjustment of a potentiometer P. This set value corresponds to the value of the frequency at which the change in amplitude variation of the signal representative of the conductivity variation of the analyzed body or medium is to be analyzed. This set value is preferably fixed with respect to the output value of the phase comparator corresponding to a zero phase.

This embodiment is well suited for determining a low-conductivity part of a body which is contains low Foucault current values leading to low energy dissipations. In fact, for variation in the amount of conductive phase leading to low variations in the quality factor, a high frequency value is preferably selected. The tuning capacity therefore exhibits a low value which is more easily disturbed by parasitic phenomena. In order not to be affected by these parasitic phenomena, the tuning frequency of the circuit is controlled by means of the system described above. This procedure allows measurements representative only of the dissipations generated by the Foucault currents to be obtained, and it enables following the way the conductive part present in the analyzed medium varies by measuring the amplitude variation, through the measurement of the amplitude of the envelope of the signal taken at the terminals of the inductive element.

Figure 3:
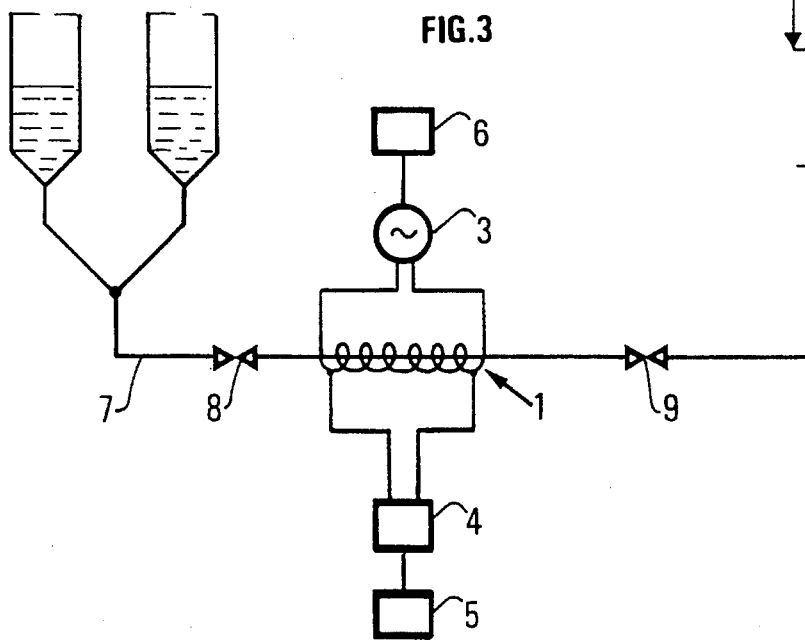
FIG. 3 shows a device according to the invention for determining the volume of the conductive phase of a fluid.

The embodiment of FIG. 3 allows determination of the amount or volume of a conductive phase in a fluid, with the fluid flowing for example through a pipe and passing at least partly in the coil.

The procedure is achieved as follows: The fluid is run into a pipe 7 controlled by two valves 8, 9, one being located upstream and the other downstream from the device, and the resonant circuit is activated according to the method described in connection with FIG. 1. The variation of the quality factor Q with time is measured by detecting device 4. The signal representative of this measurement is sent into processor 5 which analyzes it and determines for example the volume or the amount of water constituting the conductive phase of the flowing fluid. When a two-phase fluid of known volume is analyzed, the volume of the non conductive phase may also be obtained.

Figure 4A:
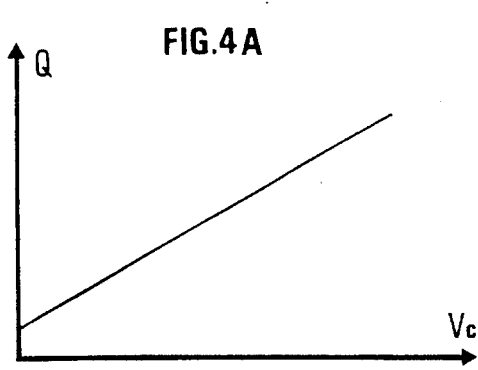
FIGS. 4A, 4B, 4C and 4D diagrammatically show experimental curves allowing the volume of the conductive phase and the velocity of the particles to be obtained.

The interpretation of the curve obtained by recording the quality factor variations is achieved by processor 5 which is programmed for carrying out the following operations:

Processor 5 compares the general shape of the curve with curves such as those shown in FIG. 4A for example, previously stored in a memory. These reference curves are obtained from previous coil calibration tests during which a fluid of controlled composition has been run through a pipe, i.e. a fluid whose proportion of the volumes of conductive phase and of non conductive phase are known at any time and for which the quality factor variations associated with changes in the proportion of the conductive phase have been recorded. The volume of the conductive phase $V_c$ at any time in the fluid flowing through pipe 7 is determined by comparison with these stored curves. It is also possible, knowing the total amount of the fluid which flowed in a pipe, to obtain the volume of the non conductive phase.

Another way of interpreting the results, when the average value of the conductivity of a fluid is known, is determining the volume of the conductive phase or part of the fluid flowing in pipe 7 from the known relation connecting the value U of the activated resonant circuit to the conductivity σ and the volume V of the conductive phase: U~ (1/σV).

Conversely, when the volume of the conductive phase of the fluid analyzed is known, processor 5 may also calculate, from the recorded data concerning the quality factor, the value of the average conductivity of the conductive phase or part of the fluid.

The total amount or total volume of the fluid which circulated in the pipe for any given time is obtained, for example, by integration of the representative function of the curve (FIG. 4A), as it is well-known.

The method according to the invention also allows complementary information to be obtained on the velocity of the conductive particulate matter. The term "particulate matter" applies to the droplets of one of the phases when the fluid is in emulsion as well as to solid particles.

Figure 4B:

The irregularities of the slope of the curve are therefore exploited (FIG. 4B). This curve has been obtained by measuring, as a function of time, the quality factor Q for a two-phase fluid made up of water for its conductive part and of oil for its non conductive part. Two constant areas separated by a slope showing irregularities may be seen in this figure. The value of the slope is representative of the change of the fluid structure, i.e. the way the amounts of conductive phase and of non conductive phase present in the fluid vary, the portion on the left of the curve representing the quality factor Q when the fluid contains 100% water or conductive phase and the right portion, 100% oil or non conductive phase.

Therefore, for a fluid comprising conductive particulate matters in a substantially non-conductive medium, the velocity spectrum of the particles or droplets is obtained by analyzing the autocorrelation function A(t) of the part of the curve showing irregularities and the average concentration of the particulate matter contained in the flowing fluid.

Figure 4D:
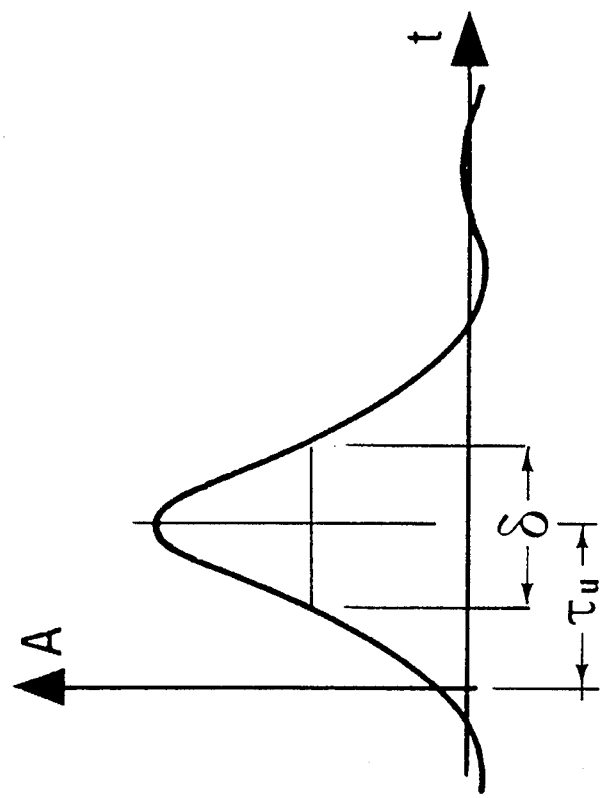
Figure 4C:
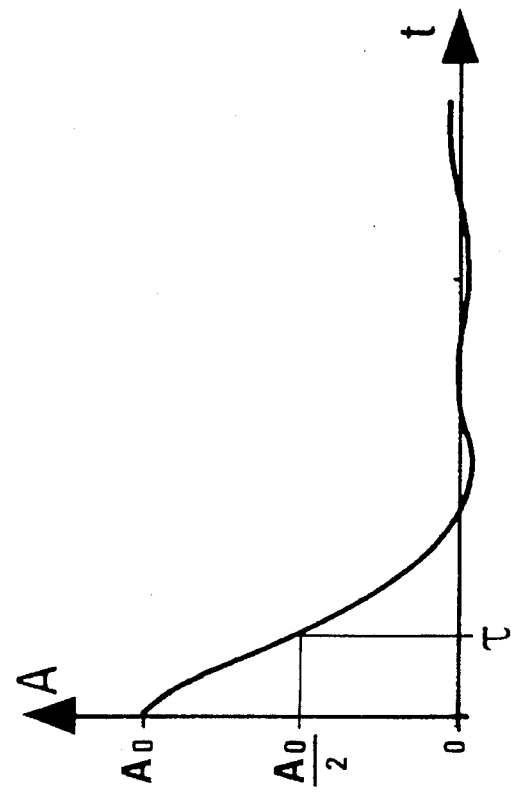

FIG. 4C shows, as a function of time, the auto-correlation function of the curve Q (t) obtained from measurements achieved on a fluid whose conductive part is water and whose non conductive part is oil. Thus, the time value $\tau$, measured for example for an amplitude at half-height of the curve is proportional to the product of the average concentration of the particles and of the inverse of the particulate matter velocity.

When the average concentration of the particulate matter is not known, this ambiguity may be removed by using two coils located at a known distance from each other.

The principle consists in measuring the signal obtained in the first coil, then the signal at the level of the second coil, and thereafter in achieving a cross-correlation of the two signals obtained previously.

FIG. 4D shows a curve obtained with this procedure. The maximum relative amplitude exhibits a lag $\sigma_d$ which is directly proportional to the velocity of the conductive particulate matter.

The width $\delta$, measured at half-height for example, of the signal gives information on the average concentration of the particulate matter.

From the velocity of the particulate matter of the conductive phase, processor 5 determines the mass flow rate of the conductive phase circulating in pipe 7 whose section is known, by means of the well-known relation:flow rate= velocity×surface area.

When the fluid is made up of several phases among which at least one is a conductive phase, and when the phases have no significant viscosity variation, i.e. when their velocities of flow are substantially equal, the measurement of the particulate matter velocity is considered representative of the velocity of the various phases contained in the fluid. Processor 5 may calculate the value of the total flow rate of the fluid circulating in pipe 7.

Figure 5:
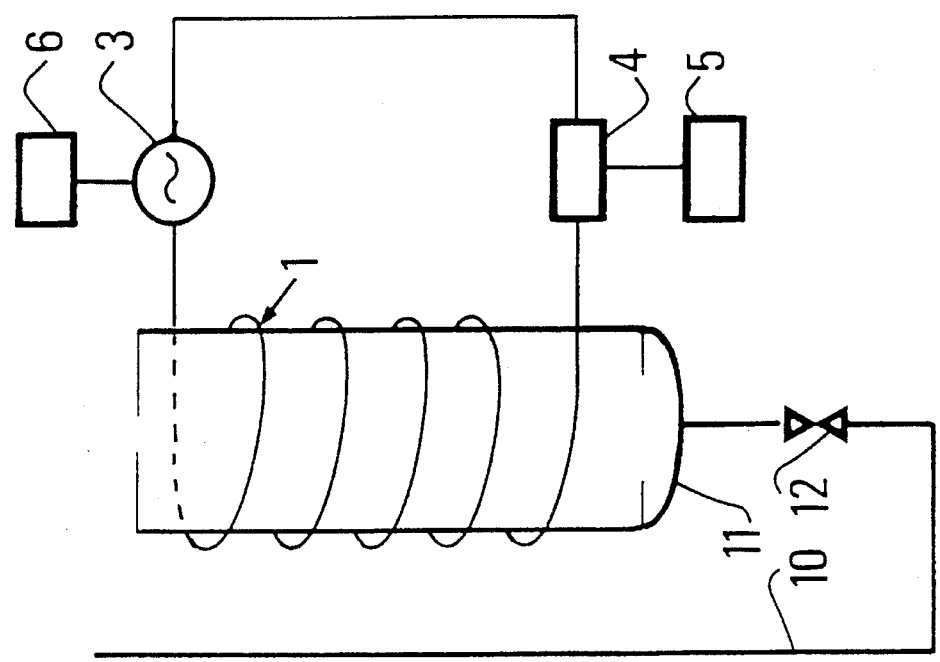
FIG. 5 shows a device for measuring the level of the conductive phase of a fluid.

FIG. 5 shows a device having a given geometry, from which the level of the conductive phase of a fluid passing at least partly in the coil constituting the inductive part of the resonant circuit is determined.

The fluid containing water and oil flows in through a pipe 10 and runs into a column 11 for example located inside the measuring coil 1. A regulating device 12 such as a valve allows the flow rate of the fluid passing in column 11 to be controlled. An alternating excitation signal, of a frequency preferably equal to the tuning frequency of the circuit, is applied to coil 1. Once the signal is applied, the value of the quality factor of the circuit is recorded by means of the detecting device 4 (FIG. 2). These data are then transmitted to processor 5. This measurement is for example performed continuously.

The level of the conductive phase is followed up by recording the variation of the quality factor Q resulting from the variation in the amount of conductive phase in the part located in the coil. The losses due to the Foucault currents in the conductive part, which are representative of the amount of conductive phase present in the fluid, cause a variation of the quality factor.

These data allow the value of the level of the water contained in the fluid to be obtained, for example by comparison with a family of experimental reference curves obtained previously.

These curves may be obtained for example by mixing together, in column 11, a conductive phase, a brine made up of water admixed with sodium chloride for example, and a non conductive phase, for example oil, and by measuring the variations of the coefficient Q of coil 1 for various proportions of oil and water and various chloride concentrations.

Figure 6:
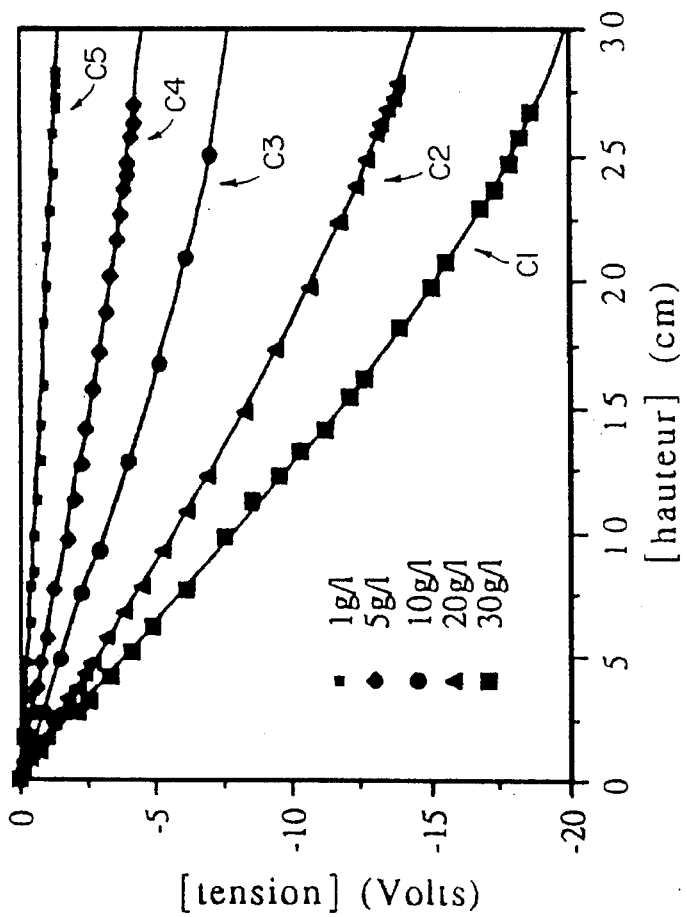
FIG. 6 shows curves obtained during measuring of the level of a fluid.

The various lines C1, C2, C3, C4, C5 of the experimental curves of FIG. 6 correspond to variable salinity values of fluids. Curves C1, C2, C3, C4, C5 correspond respectively to salinity values of 1 g/l, 5 g/l, 10 g/l, 20 g/l, 30 g/l. From the recorded data, the parameters of the analyzed water, notably the salinity of the water, and the reference curves, processor 5 determines by comparison the level of water contained in column 11 for a measured quality value $Q_o$.

Tests have shown that the measuring sensitivity of the device is about 1%.

Figure 7:
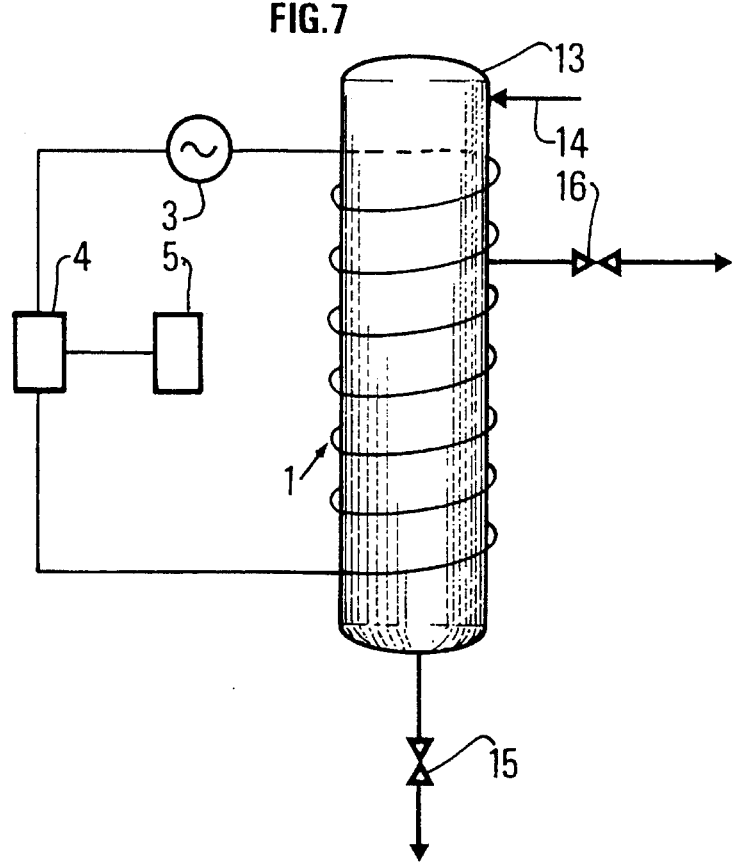
FIG. 7 shows a device according to the invention for determining the time of decantation of a fluid in emulsion.

The embodiment of FIG. 7 is particularly well suited for following up the separation of the phases of a fluid, at least one of the phases thereof being a conductive phase. This operation is also called decanting a fluid. This embodiment is notably used to test a fluid having an emulsion, for example an oil-in-water emulsion, where oil droplets are dispersed in water.

The device includes a volume 13 located preferably inside a measuring coil 1 connected to a control and processing assembly 3, 4, 5 similar to that of FIG. 5. The volume 13 is provided with an emulsion-supply line 14, a valve 15 for drawing off the water and a valve 16 for drawing off the oil.

The circuit is excited and the measuring signals are stored in processor 5. From the recorded values, processor 5 establishes for example the changing curve of the voltage U as a function of time and its slope variations, and it determines therefrom the decantation time or duration of the fluid in emulsion, at the end of which the two phases, water and oil in this example, are practically separated.

Figure 8:
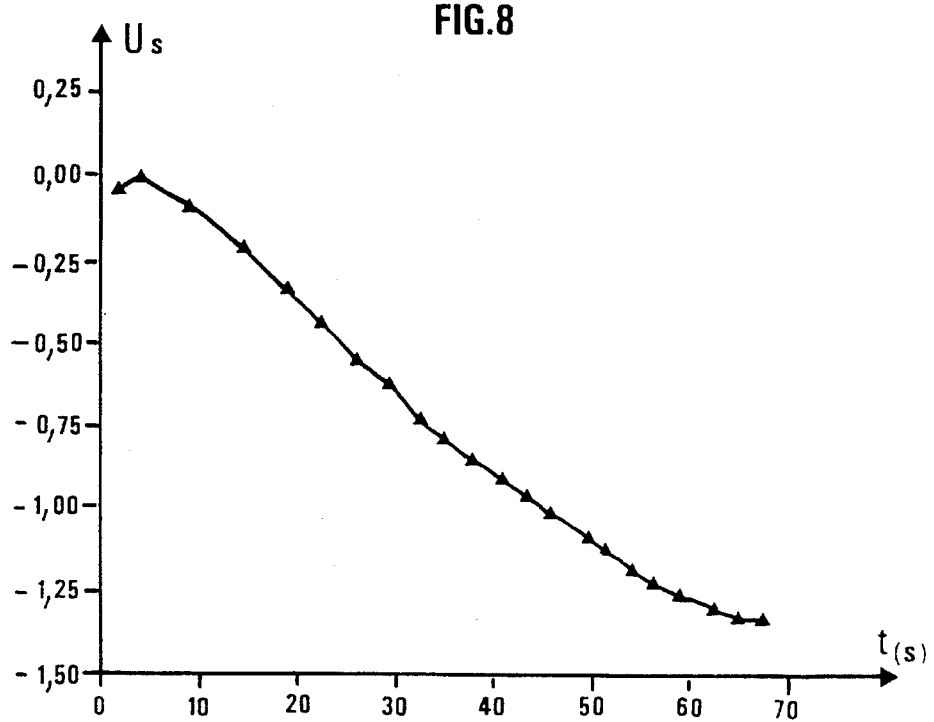
FIG. 8 shows experimental curves obtained during the determination of the time of decantation of a fluid.

FIG. 8 is an example of an experimental curve obtained during decantation tests carried out for a fluid in emulsion made up of 38% dodecane and 62% brine. The stability index of the decanting fluid may also be deduced from the slope measured at half-height for example.

Without departing from the scope of the invention, this method may be applied to a medium such as a fluid in which the non conductive phase is air or any other non conductive phase.

Similarly, without departing from the scope of the invention, the position of the excitation coil with respect to the enclosure may be changed. It may be placed inside an enclosure containing the fluid to be analyzed as well as outside and close to it.

Of course, the process and the device which have been described by way of non limitative examples may be provided with various modifications and/or additions by a person skilled in the art without departing from the scope of the invention.

We claim:

1. A method for determining a characteristic of a medium comprising:

providing a resonant circuit containing a coil which is magnetically coupled to the medium when the resonant circuit is coupled to a source of electrical current which causes the resonant circuit to resonate substantially at a resonant frequency;

coupling electrical current from the source of electrical current to the resonant circuit to produce electrical current flow in the resonant circuit at the resonant frequency and to couple a magnetic field varying at the resonant frequency emanating from the coil to the medium; and measuring an amplitude of an envelope of electrical current flowing in the resonant circuit and processing the measured amplitude to determine the characteristic of the medium with any conductivity of the medium providing a path for electrical current to flow in the medium which current flow is induced by the magnetic field and which effects the measured amplitude of the envelope.

2. A method in accordance with claim 1 wherein:

the source of electrical current produces a periodic excitation signal which is applied to the resonant circuit with a frequency of the periodic excitation signal being equal to the resonant frequency.

3. A method in accordance with claim 1 further comprising:

determining that the medium is partially electrically conductive by measuring the amplitude of the envelope of the current flowing in the resonant circuit with the measured amplitude being a function of the partial conductivity of the medium.

4. A method in accordance with claim 3 wherein:

the source of the electrical current produces a continuous signal coupled to the resonant circuit.

5. A method in accordance with claim 3 wherein:

the source of electrical current produces a periodic excitation signal which is applied to the resonant circuit with a frequency of the periodic excitation signal being substantially equal to the resonant frequency.

6. A method in accordance with claim 3 wherein:

the medium is a fluid having a conductive phase of a known volume and a non-conductive phase; and further comprising determining an average conductivity of the conductive phase.

7. A method in accordance with claim 3 wherein:

the medium is a fluid having a conductive phase of a known conductivity and at least one non-conductive phase; and further comprising determining a volume of the conductive phase.

8. A method in accordance with claim 3 wherein:

the medium is a fluid having plural phases with at least one of the phases being conductive with the fluid flowing in a pipe and being magnetically coupled to the magnetic field emanating from the coil; and further comprising:

determining a mass flow of the conductive phase.

9. A method in accordance with claim 8 wherein:

the plural phases have substantially identical flow velocities; and further comprising determining a volume flow rate of the fluid.

10. A method in accordance with claim 3 wherein:

the medium is a fluid having at least two phases with one of the phases being conductive and the fluid being of known volume contained in a vessel with at least part of the fluid being magnetically coupled to the magnetic field emanating from the coil; and further comprising determining a level of the conductive phase of the fluid in the vessel.

11. A method in accordance with claim 3 wherein:

the fluid has two phases mixed in an emulsion with at least part of the fluid being magnetically coupled to the magnetic field emanating from the coil; and further comprising determining a decantation time of the fluid.

12. A method in accordance with claim 1 wherein:

the source of the electrical current produces a continuous signal coupled to the resonant circuit.

13. An apparatus for determining a characteristic of a partially conductive medium comprising:

a resonant circuit including a coil for producing a magnetic field for magnetic coupling to the partially conductive medium;

a signal source, coupled to the resonant circuit, for generating an excitation signal which produces an electrical current flow in the coil at a resonant frequency which produces the magnetic field varying at the resonant frequency which is magnetically coupled to the medium;

a detector for measuring an amplitude of an envelope of electrical current flow in the coil with the amplitude of the envelope being a function of a conductivity of the partially conductive medium; and a processor coupled to the detector, for processing the detected amplitude of the envelope for determining from the measured amplitude the characteristic of the partially conductive medium.

14. An apparatus in accordance with claim 13 wherein:

the signal source generates a continuous excitation signal which is coupled to the resonant circuit.

15. An apparatus in accordance with claim 14 wherein:

the coil has at least one turn which surrounds the medium.

16. An apparatus in accordance with claim 15 wherein:

the coil comprises a double winding which generates the magnetic field having a uniform distribution inside the double winding.

17. An apparatus in accordance with claim 14 wherein:

the coil comprises a double winding which generates the magnetic field having a uniform distribution inside the double winding.

18. An apparatus in accordance with claim 14 further comprising:

a phase lock loop, coupled to the resonant circuit and the signal source, for maintaining the excitation signal substantially at the resonant frequency of the resonant circuit.

19. An apparatus in accordance with claim 13 wherein:

the signal source generates a periodic excitation signal having a periodic frequency substantially equal to the resonant frequency.

20. An apparatus in accordance with claim 19 wherein:

the coil comprises a double winding which generates the magnetic field having a uniform distribution inside the double winding.

21. An apparatus in accordance with claim 19 further comprising:

a phase lock loop, coupled to the resonant circuit and the signal source, for maintaining the excitation signal substantially at the resonant frequency of the resonant circuit.

22. An apparatus in accordance with claim 13 wherein:

the coil has at least one turn which surrounds the medium.

23. An apparatus in accordance with claim 22 wherein:

the coil comprises a double winding which generates the magnetic field having a uniform distribution inside the double winding.

24. An apparatus in accordance with claim 13 wherein:

the coil comprises a double winding which generates the magnetic field having a uniform distribution inside the double winding.

25. An apparatus in accordance with claim 13 further comprising:

a phase lock loop, coupled to the resonant circuit and the signal source, for maintaining the excitation signal substantially at the resonant frequency of the resonant circuit.

* * * * *